US00PP12606P2

(12) United States Plant Patent
Hoek

(10) Patent No.: US PP12,606 P2
(45) Date of Patent: May 7, 2002

(54) CHRYSANTHEMUM PLANT NAMED 'DELISTAR YELLOW'

(75) Inventor: Jan Hoek, 's-Gravenzande (NL)

(73) Assignee: Deliflor B.V., Maasdijk (NL)

( * ) Notice: Subject to any disclaimer, the term of this patent is extended or adjusted under 35 U.S.C. 154(b) by 0 days.

(21) Appl. No.: 09/653,606

(22) Filed: Aug. 31, 2000

(51) Int. Cl.[7] ..... A01H 5/00
(52) U.S. Cl. ..... Plt./289
(58) Field of Search ..... Plt./289

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Delistar Yellow', characterized by its large quilled spider double-type inflorescences with yellow-colored ray florets; inflorescences with numerous ray florets and few disc florets; dark green foliage; strong flower stems; low number of inflorescences per flowering stem; short response time; unattractive to leafminers; excellent postproduction longevity; and tolerance to low light.

2 Drawing Sheets

BACKGROUND OF THE INVENTION

The present invention relates to a new and distinct cultivar of Chrysanthemum plant, botanically known as *Dendranthema grandiflora* and referred to by the cultivar name Delistar Yellow.

The new Chrysanthemum was discovered by the Inventor in a controlled environment in 's-Gravenzande, The Netherlands in April, 1999, as a naturally-occurring whole plant mutation of the *Dendranthema grandiflora* cultivar Delistar, disclosed in U.S. Plant Pat. No. 11,964. The new Chrysanthemum was observed as a single plant in a group of flowering plants of the parent cultivar. The selection of this plant was based on its unique ray floret color.

Asexual reproduction of the new Chrysanthemum by terminal cuttings harvested in 's-Granvenzande, The Netherlands, has shown that the unique features of this new Chrysanthemum are stable and reproduced true to type in successive generations.

BRIEF SUMMARY OF THE INVENTION

The cultivar Delistar Yellow has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Delistar Yellow'. These characteristics in combination distinguish 'Delistar Yellow' as a new and distinct cultivar:

1. Large quilled spider double-type inflorescences with yellow ray florets; typically grown as a single inflorescence per flowering stem.
2. Numerous ray florets and few disc florets; disc florets typically inconspicuous.
3. Dark green foliage.
4. Strong flower stems.
5. Low number of inflorescences per flowering stem which reduces the amount of disbudding required.
6. Short response time.

7. Unattractive to leafminers.
8. Excellent postproduction longevity.
9. Tolerant to low light conditions, can be grown without the benefit of supplemental lighting.

Plants of the new Chrysanthemum differ from plants of the parent cultivar, Delistar, primarily in ray floret color. In addition, plants of the new Chrysanthemum have larger inflorescences than plants of the cultivar Delistar.

Plants of the new Chrysanthemum can be compared to plants of the cultivar Spider Yellow, not patented. In side-by-side comparisons conducted by the Inventor in 's-Granvenzande, The Netherlands, plants of the new Chrysanthemum and the cultivar Spider Yellow differ in the following characteristics:

1. Plants of the new Chrysanthemum flower at least seven days earlier than plants of the cultivar Spider Yellow.
2. Plants of the new Chrysanthemum have fewer inflorescences per flowering stem and therefore more economical to grow as a single inflorescence per stem than plants of the cultivar Spider Yellow.
3. Ray floret corolla tubes of plants of the new Chrysanthemum are more coarse than ray floret corolla tubes of plants of the cultivar Spider Yellow.
4. Inflorescences of plants of the new Chrysanthemum develop few conspicuous disc florets whereas inflorescences of plants of the cultivar Spider Yellow develop conspicuous disc florets.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Chrysanthemum.

The photograph on the first sheet comprises a side perspective view of a typical flowering stem of 'Delistar Yellow'.

The photograph at the top of the second sheet comprises a close-up view of a typical inflorescence of 'Delistar Yellow'.

The photograph at the bottom of the second page comprises a close-up view of the upper and lower surfaces of typical leaves of 'Delistar Yellow'.

DETAILED BOTANICAL DESCRIPTION

In the following description, color references are made to The Royal Horticultural Society Colour Chart except where general terms of ordinary dictionary significance are used. The following observations and measurements describe plants grown in 's-Gravenzande, The Netherlands, under commercial practice in a glass-covered greenhouse. Plants were initially given short nights followed by long nights to induce flower initiation and development. Average day and night temperatures were 18 and 19° C., respectively.

Botanical classification: *Dendranthema grandiflora* cultivar Delistar Yellow.

Commercial classification: Quilled spider double-type Chrysanthemum typically grown as a cut flower.

Parentage: Naturally-occurring whole plant mutation of *Dendranthema grandiflora* cultivar Delistar, disclosed in U.S. Plant Pat. No. 11,964.

Propagation:

*Type.*—Terminal tip cuttings.

*Time to initiate roots, summer.*—About 10 days at 20° C.

*Time to initiate roots, winter.*—About 14 days at 20° C.

*Root description.*—Fine, fibrous and well-branched.

Plant description:

*Appearance.*—Herbaceous quilled spider double-type cut Chrysanthemum; typically grown as a single inflorescence per flowering stem. Upright with strong stems.

*Growth rate.*—Moderate; moderately vigorous.

*Crop time.*—For cut flowers, about 78 and 117 days are required to produce flowering stems during the summer and winter, respectively.

*Stem description.*—Length: About 70 to 80 cm. Strength: Strong. Aspect: Upright. Color: 147B.

*Foliage description.*—Arrangement: Alternate. Quantity of leaves per main stem: About 12 to 15. Length: About 10 cm. Width: About 6.5 cm. Apex: Acute. Base: Acute. Margin: Palmately lobed. Texture: Rough; both surfaces pubescent. Petiole length: About 3 cm. Color: Young foliage, upper surface: 147A. Young foliage, lower surface: 137A. Mature foliage, upper surface: 147A. Mature foliage, lower surface: 137B. Venation, upper and lower surfaces: 137C. Petiole: 137C.

Inflorescence description:

*Appearance.*—Quilled spider double-type inflorescence form. Inflorescences borne on terminals, arising from leaf axils. Ray and disc florets arranged acropetally on the receptacle.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about seven weeks later.

*Postproduction longevity.*—Inflorescences will maintain good substance and form for about three weeks after harvesting.

*Quantity of inflorescences per flowering stem.*—About 6 to 9.

*Inflorescence size.*—Diameter: Large, about 15.5 cm. Depth (height): About 4.5 cm. Diameter of disc: About 1 cm; typically inconspicuous.

*Inflorescence buds.*—Length: About 1.25 cm. Diameter: About 1.4 cm. Shape: Flat spherical.

*Ray florets.*—Length, fully developed: About 7.5 cm. Width, fully developed: About 6 mm. Shape: Fused, tubular; quilled. Texture: Smooth, glabrous. Number of ray florets per inflorescence: About 300. Color: When opening, upper and lower surfaces: 6D. Mature, upper surface: 6C; fading to 5D. Mature, lower surface: 6D; fading to 5D.

*Disc florets.*—Shape: Oblong, tubular. Length: About 4 mm. Width: About 1 mm. Number of disc florets per inflorescence: Few, about 25; typically inconspicuous. Color: Immature: Greenish white; no color similar in R.H.S. Colour Chart. Mature: Apex, 1A; base, greenish white; no color similar in R.H.S. Colour Chart.

*Peduncles.*—Length, terminal peduncle: About 9 cm. Length, fourth peduncle: About 14 cm. Diameter: About 2.5 mm. Angle: About 60 to 80° to main stem. Texture: Pubescent. Color: 147B.

*Reproductive organs.*—Androecium: Present on disc florets only. Anther color: 15B. Pollen: 16B. Gynoecium: Present on both ray and disc florets. Stigma length: About 5 mm. Stigma width: About 0.3 mm. Stigma color: Apex, 9B; base, close to 150D.

*Seed.*—Seed production has not been observed.

Disease resistance: Resistance to known Chrysanthemum diseases has not been observed on plants of the new Chrysanthemum.

Insect attractiveness: Plants of the new Chrysanthemum have been shown to be unattractive to leafminers (*Lyriomyza trifolii*).

It is claimed:

1. A new and distinct cultivar of Chrysanthemum plant named 'Delistar Yellow', as illustrated and described.

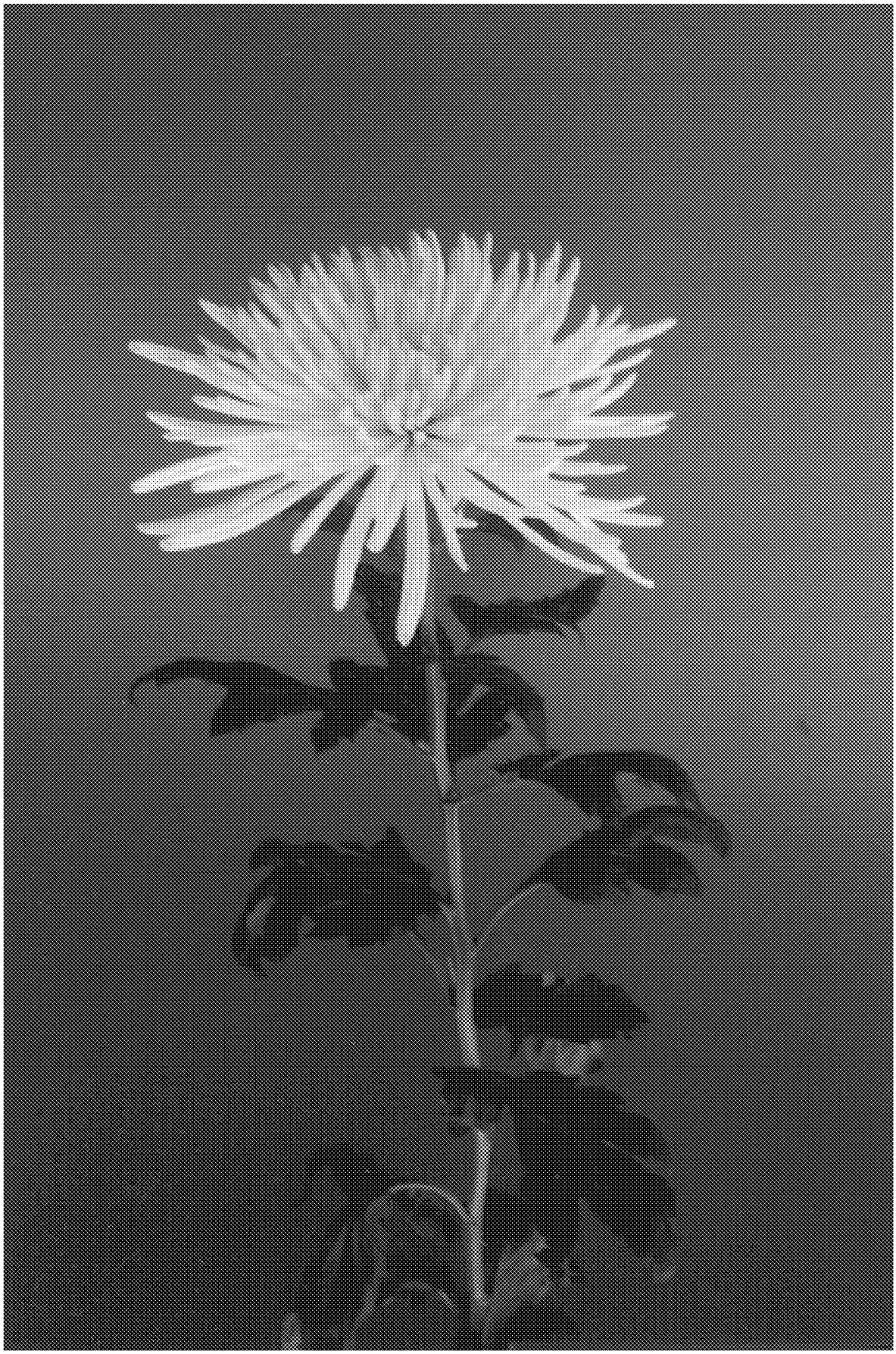

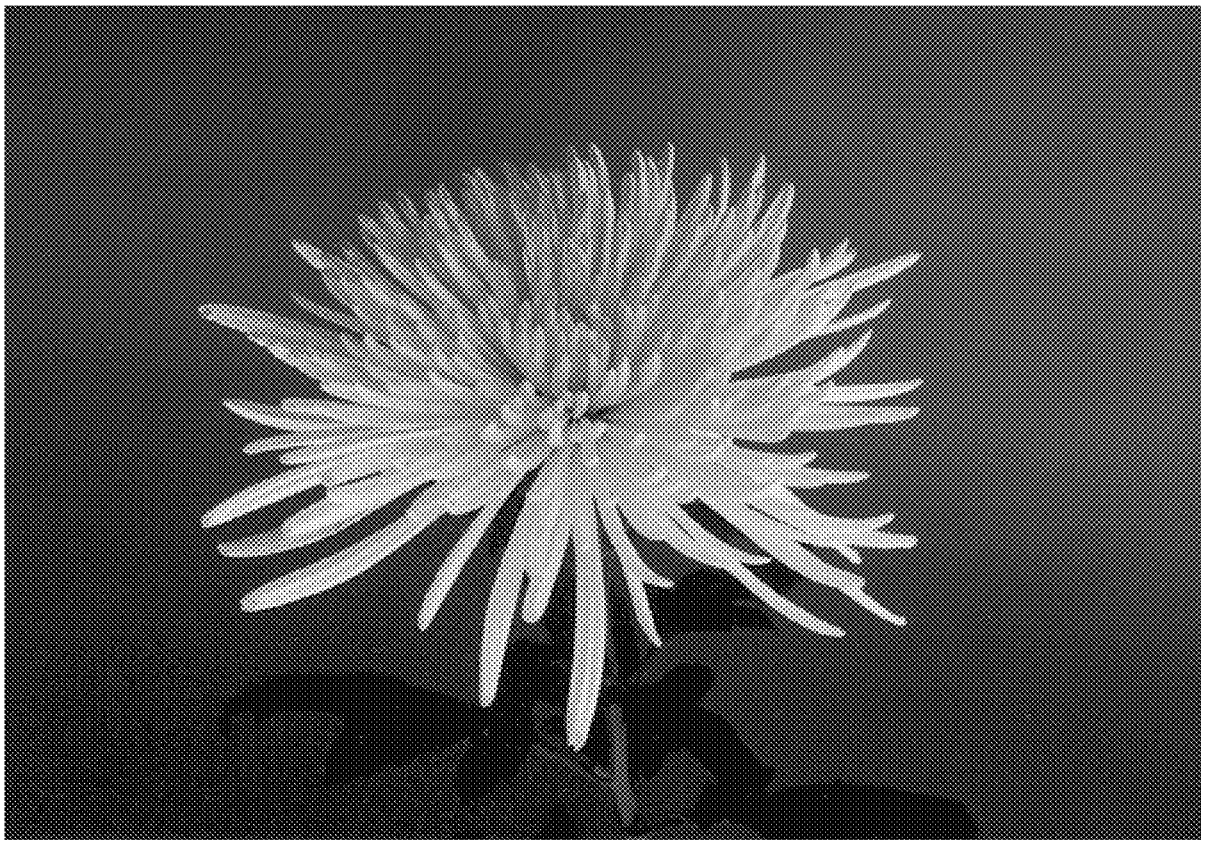
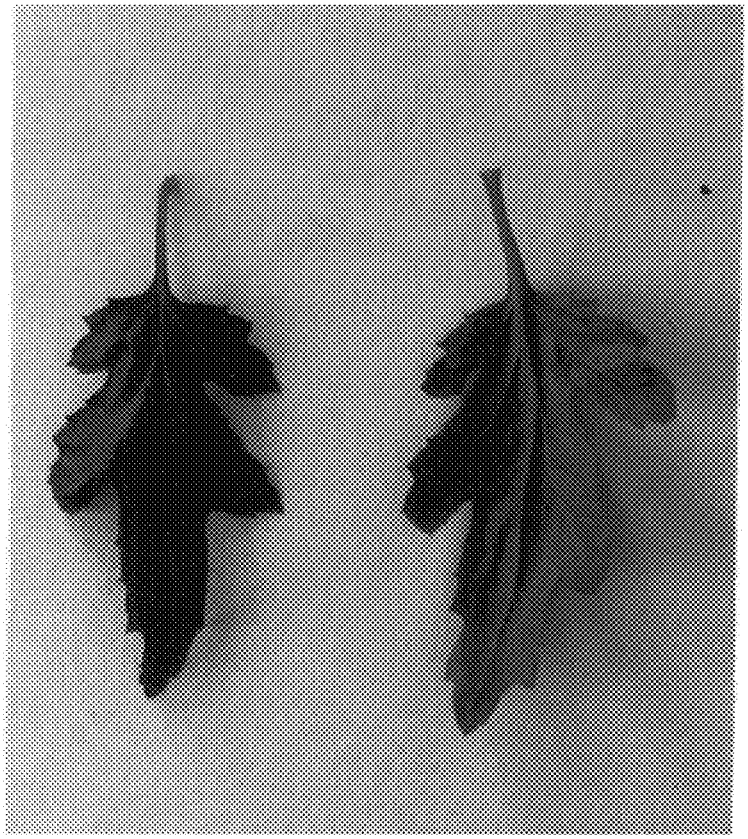

* * * * *